United States Patent [19]

Focella et al.

[11] 4,340,736

[45] Jul. 20, 1982

[54] DIAGNOSTIC TEST FOR BARBITURATES

[75] Inventors: Antonino Focella, Clifton; John E. Heveran, Fairfield; Sidney Teitel, Clifton; Manfred Weigele, North Caldwell, all of N.J.

[73] Assignee: Hoffmann-La Roche Inc., Nutley, N.J.

[21] Appl. No.: 100,328

[22] Filed: Dec. 5, 1979

Related U.S. Application Data

[60] Continuation of Ser. No. 901,382, May 1, 1978, abandoned, which is a division of Ser. No. 690,123, May 26, 1976, Pat. No. 4,101,549.

[51] Int. Cl.³ .......................................... C07D 239/62
[52] U.S. Cl. .................................................. 544/301
[58] Field of Search ........................................ 544/301

[56] References Cited

U.S. PATENT DOCUMENTS 4,101,549 7/1978 Focella et al. ...................... 544/301

Primary Examiner—Paul M. Coughlan, Jr.
Attorney, Agent, or Firm—Jon S. Saxe; Bernard S. Leon; James H. Callwood

[57] ABSTRACT

Aminoaryl esters and amino-lower alkyl amides of carboxy substituted barbiturates are linked via an amide linkage to carboxylated latex polymers to form reagents which are useful in a sensitive diagnostic test to detect the presence of barbiturates in body fluids.

2 Claims, No Drawings

DIAGNOSTIC TEST FOR BARBITURATES

This is a continuation of application Ser. No. 901,382, filed May 1, 1978, now abandoned, which in turn is a divisional of U.S. patent application Ser. No. 690,123, filed May 26, 1976, now U.S. Pat. No. 4,101,549.

BACKGROUND OF THE INVENTION

The large increase in the abuse of therapeutic agents, particularly the barbiturates, by the general population as well as military personnel, has brought with it a substantial need to improve analytical techniques for the determination of such agents in biological fluids. In many instances, medical treatment centers are faced with the immediate need for determining the identity of a barbiturate taken by a patient who is unable, being in a comatose condition, or unwilling to supply such information to the treating physician. Early procedures involved the identification of barbiturates by extraction and thin-layer, gas chromatographic and spectrophotometric methods. These techniques have the disadvantages of being relatively time-consuming, laborious and lacking great sensitivity. Recently, a rapid and sensitive immunoassay procedure involving the reaction between antibodies and barbiturate antigen was described by S. Spector in U.S. Pat. No. 3,766,162 and by S. Spector and E. J. Flynn in Science, 174, 1037 (1971). This procedure, however, requires sophisticated and expensive equipment, such as scintillation counters. Therefore, it would be desirable to develop a rapid and highly sensitive assay for detecting the presence of barbiturates in biological fluids which would not require sophisticated equipment and could be easily performed on site by laboratory technicians having a minimum of training.

BRIEF DESCRIPTION OF THE INVENTION

The present invention relates to a novel class of barbiturate derivatives, namely, aminoaryl esters and amino-lower alkyl amides of carboxy substituted barbiturates, which esters and amides may be covalently coupled via an amide linkage to a carboxylated latex polymer. The barbiturate thus linked to the latex polymer by means of the linking group can then be utilized as a reagent in a sensitive diagnostic assay for the presence of barbiturates in biological fluids. This assay method is dependent upon the well known binding of antigen to antibodies specific therefor, which is manifested by an insolubilization or agglutination followed by flocculation. When either the antigen or the antibody is linked to a suitable polymer such as a latex polymer, as hereinafter described, the detection of the antigen-antibody binding by means of agglutination is significantly enhanced by means of the latex so that such agglutination reaction is easily visualized by the naked eye.

The general technique of utilizing latex particles as carriers for antigens or antibodies for easy visualization of the antigen-antibody reaction has been previously described in the literature, for example, U.S. Pat. No. 3,857,931.

The starting materials which are used for the preparation of the latex reagents of the present invention are aminoaryl esters and amino-lower alkyl amides of carboxy substituted barbiturates. As used herein, the expression "lower alkyl" is meant to include straight and branched-chain saturated hydrocarbon radicals having from 2 to 8 carbon atoms, inclusive, such as ethyl, propyl, n-butyl, iso-butyl and the like. The term "aryl" denotes an aromatic radical derived from an unsubstituted or substituted arene and includes phenyl, naphthyl, halophenyl, tolyl, anisyl, nitrophenyl, hydroxyphenyl and the like. The term "halide" denotes iodide, bromide and chloride.

The barbiturates useful for binding to latex polymers are those having free carboxylic acid groups. The barbiturate of particular preference in the practice of the present invention is 5-allyl-5-(1-carboxy-isopropyl)barbituric acid (allonalcarboxylic acid) since it has a carboxylic acid group in the sidechain and is readily obtainable. Thus, particularly preferred reagents are aminoaryl esters and amino-lower alkyl amides of the carboxylic acid group of allonalcarboxylic acid. However, the present assay, as hereinafter described, will detect barbiturates with or without free or functionalized carboxylic acid groups, such as barbital, phenobarbital, amobarbital, butabarbital, pentobarbital, etc.

The aminoaryl esters and amino-lower alkyl amides of carboxy substituted barbiturates, as described above, are conveniently prepared from carboxy substituted barbiturates. Using allonalcarboxylic acid as an example, one can conveniently introduce the requisite aminoaryl or the amino-lower alkyl moiety by methods well known in the art. Thus, for the preparation of aminoaryl esters of the carboxy substituted barbiturates, one can esterify allonalcarboxylic acid with, for example, p-nitrophenol to afford 5-allyl-5-(1-p-nitrophenyloxycarbonyl-isopropyl)barbituric acid which one can then reduce to 5-propyl-5-(p-aminophenyloxycarbonyl-isopropyl) barbituric acid.

The esterification is performed in the presence of a condensing agent dissolved in an inert organic solvent. Suitable condensing agents include carbodiimides such as N,N'-diphenylcarbodiimides and N,N'-dicyclohexylcarbodiimies. Suitable inert organic solvents include polar aprotic solvents such as N,N-dimethylformamide, dimethylsulfoxide and hexamethylphosphoramide alone or admixed with non-polar aprotic solvents such as acetone, acetonitrile and ethyl acetate. A particularly preferred condensing agent is N,N'-dicyclohexylcarbodiimide and a particularly preferred organic solvent system is N,N-dimethylformamide-ethyl acetate.

The temperature of the esterification reaction is not narrowly critical. The reaction may be carried out between about 0° and 50° C., most preferably at about 0° to 25° C.

The reduction is performed by treating the nitroester, so obtained, dissolved in a suitable inert organic solvent, preferably an alkanol such as methanol, ethanol, or 2-propanol, with hydrogen in the presence of a suitable hydrogenation catalyst until the cessation of the uptake of hydrogen. Included among suitable hydrogenation catalysts are platinum, palladium, rhodium, ruthenium and nickel, unsupported or supported on carriers such as carbon, silica, alumina and the like. A particularly preferred hydrogenation catalyst is 10% palladium-on-carbon. While the temperature and pressure at which the hydrogenation is accomplished is not critical, it is preferred to carry out the reaction at about room temperature and about atmospheric pressure.

For the preparation of amino-lower alkyl amides of carboxy substituted barbiturates, one can aminate allonalcarboxylic acid with, for example, 1,4-diaminobutane to afford 5-allyl-5-[1-(4-aminobutylcarbamoyl)-isopropyl]barbituric acid.

The amination is performed in the presence of a condensing agent dissolved in an inert organic solvent. Suitable condensing agents include carbodiimides such as N,N'-diphenylcarbodiimide and N,N'-dicyclohexylcarbodiimide and carbonyldiimidazoles such as 1,1'-carbonyldiimidazole. Suitable inert organic solvents are ethereal solvents such as monoglyme, diglyme, dioxane and tetrahydrofuran. A particularly preferred condensing agent is 1,1'-carbonyldiimidazole. A particularly preferred inert organic solvent is tetrahydrofuran.

The temperature at which the amination is carried out is not narrowly critical. A reaction temperature within the range of about 0° to about the boiling point of the solvent is preferred, a reaction temperature of about 25° C. being most preferred.

The carboxy substituted barbiturates are also conveniently prepared by methods well known to a chemist of ordinary skill in the art. For example, the carboxy substituted barbiturates can be readily prepared by reductive alkylation of barbituric acid with an aldehydo- or keto-ester followed by alkylation and saponification of the ester group of the resulting 5,5-disubstituted-barbituric acid.

The reductive alkylation is conducted by treating barbituric acid and an aldehydo- or keto-ester such as ethyl formylacetate, ethyl acetoacetate and ethyl levulinate, with hydrogen in the presence of a metal hydrogenation catalyst to afford a 5-monosubstituted barbituric acid derivative. Suitable metal catalysts are nickel and the nobel metals such as platinum, palladium, rhodium, ruthenium and so forth. The catalysts are normally employed in finely divided form and may be either unsupported or present on a suitable inert carrier such as carbon, aluminum, silica, calcium carbonate and the like. A particularly preferred catalyst is 10% palladium-on-carbon.

As solvents for the reductive alkylation, there may be mentioned alcohols such as methanol, ethanol, 2-propanol and the like, and esters such as ethyl acetate and so forth.

While the reductive alkylation may be performed over a wide range of temperatures and pressures from, for example, about room temperature to about 150° C. and about atmospheric pressure to about 1000 psi, it is preferable to employ a reaction temperature of about 90° to about 100° C. and a pressure of about 700 psi.

The alkylation step is accomplished by treating the monosubstituted barbituric acid derivative with an alkylating agent such as methyl halide, propyl halide, allyl halide, hexyl halide, cyclohexenyl halide and the like, in a suitable inert solvent in the presence of a base to afford a 5,5-disubstituted barbituric acid derivative. Suitable solvents include, among others, alcohols such as methanol, ethanol, 2-propanol and the like, water and mixtures of water and alcohols. Suitable bases are alkali metal and alkaline earth hydroxides such as sodium and potassium hydroxide and calcium hydroxide, and alkali metal alkoxides such as sodium methoxide, potassium ethoxide and potassium tertiary-butoxide. A particularly preferred base and solvent system is about 20% aqueous sodium hydroxide. The alkylation may be conducted over a temperature range of from about 10° to about 80° C., most preferably between about 25° to 60° C.

The saponification step is conducted by treating the disubstituted barbituric acid derivative with an aqueous acid such as hydrochloric acid, hydrobromic acid, dilute sulfuric acid and the like, at an elevated temperature. For this conversion, aqueous hydrochloric acid having a normality of about 1 and a reaction temperature of about the reflux temperature of the reaction mixture is preferred.

In order to prepare the diagnostic reagent useful for the practice of the present invention, aminoaryl esters and amino-lower alkyl amides of carboxy substituted barbiturates are covalently bonded by means of an amide linkage to a latex polymer containing carboxyl groups.

Suitable latex polymers for this purpose are carboxylated styrene butadienes, carboxylated polystyrenes, acrylic acid polymers and the like. Among the commercial latex polymers which are included in the aforementioned classes are Dow 421, Dow 816, Dow 620, Fluka 241 and Dow 241. Dow batch 1721, a latex polymer of the polystyrene type having a particle size of about 0.2 to about 0.3 microns, percent solid composition of about 8 to about 12% and a specific gravity of about 1.02, is also suitable.

Particularly preferred polymers are carboxylated styrene butadiene copolymers, preferably Fluka 241 or Dow 241. Suitable latex carrier particles are generally supplied commercially as an aqueous latex suspension, usually in concentrations of about 5 to about 60% solids. These polymers are water insoluble, have a particle size in the range from about 0.01 to about 0.9 microns, preferably between about 0.1 and about 0.3 microns, and a specific gravity near that of water enabling them to remain in aqueous suspension. The particles should have sufficient surface charge density so that when coupled to the aminoaryl esters and amino-lower alkyl amides of carboxy substituted barbiturates, their repulsive forces are enough to prevent aggregation.

The aminoaryl esters and amino-lower alkyl amides of carboxy substituted barbiturates are coupled to the carboxylated latex polymers by means of an amide linkage initiated in the presence of a water soluble carbodiimide condensing agent. The degree of coupling is dependent upon the density of the reactive groups in the polymer. The density of the reactive groups is not critical to the operability of this invention, as long as a sufficient number of reactive groups are present to provide coupling of a sufficient amount of barbiturate moiety to be useful in a diagnostic test. However, a suitable density would be in the range of from about 1 to about 5%, preferably about 3%, by weight. The coupling reaction with carbodiimides is described in detail in U.S. Pat. No. 3,857,931.

Once the latex coupled product is formed, it can be utilized in specific diagnostic tests for the detection of barbiturates. It can be used in any convenient concentration, depending upon the specific test and samples involved. However, concentrations of from about 0.1 to about 2% by weight of latex solids are suitable and the preferred concentrations are from about 0.3 to about 1.5% by weight.

In a typical test, a measured amount of antiserum against barbiturates is mixed with a barbiturate free body fluid, for example, serum, saliva or urine. Then, a measured amount of aminoaryl or amino-lower alkyl barbiturate coupled latex is added and the mixture is allowed to incubate at a slightly elevated temperature, e.g., 37° C., for a period of time, for example, from about 1 to about 3 hours, preferably for about 2 hours. The pH of the test mixture is suitably in the range of from about pH 5.0 to 8.5, most preferably about 6.5 to 7.5. After the incubation, flocculation or agglutination of the latex particles is noted. The concentration and quantity of both the antiserum and the latex complex are adjusted to produce a strong flocculation, and the minimum concentrations of both reagents which produce a strong flocculation are determined. The mixture of antiserum against barbiturate and barbiturate free body fluid may be incubated at a slightly elevated temperature, e.g., 37° C., prior to the addition of the aminoaryl or amino-lower alkyl barbiturate coupled latex.

The antisera which may be used in the present diagnostic test are antisera specific for barbiturates, such as secobarbital and pentobarbital. The preparation of such antisera is described in U.S. Pat. No. 3,766,162 and in Science, 174, 1037 (1971).

After the control system is set up, as described above, various amounts of barbiturates, e.g., secobarbital, pentobarbital, butabarbital, amobarbital, phenobarbital and barbital are dissolved in barbiturate free body fluid. The minimum amount of barbiturate required to inhibit the flocculation is noted. This quantity will depend both upon the concentration and the amount of body fluid added, as well as upon the concentration and the strength of the antiserum utilized in the test.

In a preferred test, the quantities and concentrations are adjusted so that approximately 400–500 microliters of serum or urine containing between about 100 and 200 nanograms of barbiturate per milliliter (total of between 40–50 and 80–100 nanograms of barbiturate) will be just sufficient to inhibit flocculation. Once the test has been standardized with one type of body fluid, for example, urine, another type of body fluid, for example, serum, should not be substituted, and a separate standard must be set up for this.

Since the presence of flocculation is easily visualized by the naked eye, the present test serves as an extremely sensitive assay method for the detection of barbiturates, such as secobarbital, pentobarbital, butabarbital, amobarbital, phenobarbital and barbital. Thus, once the test has been standardized as mentioned above, the presence of nanogram quantities of these barbiturates in body fluids can easily be detected by noting the inhibition of flocculation caused by the presence of such barbiturates in the body fluid, as compared with the flocculation resulting when barbiturate free body fluid is employed.

The test can be standardized so that a medically and statistically meaningful cut-off point is established. Thus, quantities of barbiturates in body fluid greater than this amount will cause inhibition of flocculation (a positive test for the presence of such drug in the body fluid) and quantities less than this amount will not inhibit flocculation (a negative test).

The above described reagents can be conveniently packaged for commercial purposes, e.g., in a diagnostic reagent kit containing two separate containers: one with the antiserum against barbiturates and the other with the aminoaryl esters or amino-lower alkyl amides of carboxy substituted barbiturates bonded via an amide linkage to latex particles containing carboxyl groups, most preferably in aqueous suspension.

The aminoaryl esters and amino-lower alkyl amides of carboxy substituted barbiturates can also be linked to immunogenic carrier materials such as proteins or polypeptides by means of an amide linkage to afford antigens which are useful for the elicitation of antibodies specific for barbiturates. The method of linkage to immunogenic carrier materials, as well as the elicitation of antibodies, are generally described in U.S. Pat. No. 3,766,162.

The invention is further explained and illustrated in the following examples. All temperatures are in degrees Centigrade.

EXAMPLE 1

5-(1-Ethoxycarbonyl-isopropyl)barbituric acid

A mixture of 200 g. of barbituric acid, 215 g. of ethyl acetoacetate, 10 g. of 10% Pd-C and 400 ml. of methanol was placed into a 2 liter glass lined reaction vessel and hydrogenated at 90°–100° and 700 psi for 20 hours. Two liters of water were added to the suspension and the mixture was heated to effect solution. The catalyst was removed by filtration and the filtrate was cooled overnight. The crystals were collected to yield 209 g. of the ester, m.p. 160°–162°. The mother liquor was evaporated in vacuo and the residue was suspended, with stirring, in a small volume of boiling ethyl acetate. The solution was allowed to cool to room temperature and unreacted barbituric acid was collected. An additional 65.2 g. (total yield 87.6%, based on recovered barbituric acid) of the ester was obtained from the filtrate. It had mp. 160°–162°.

EXAMPLE 2

5-Allyl-5-(1-ethoxycarbonyl-isopropyl)barbituric acid

Into a one liter three-neck flask equipped with mechanical stirrer, reflux condenser and a dropping funnel, were placed 100 g. of 5-(1-ethoxycarbonyl-isopropyl)-barbituric acid, 100 mg. of calcium sulfate, 50 mg. of copper dust and 500 ml. of water. The mixture was stirred at room temperature for 15 minutes and 53.6 g. of allyl bromide were added in one portion followed by the dropwise addition of 125 ml. of 20% sodium hydroxide over 45 minutes at 50°–55°. After stirring at 50°–55° for 3 hours, the reaction mixture was cooled to about 30° and an additional 26.8 g. of allyl bromide were added in one portion. The reaction mixture was heated with stirring, for 90 minutes, and a solution (65–70 ml.) of 20% sodium hydroxide was then added at a rate such that the reaction mixture was always slightly alkaline. The mixture was cooled to room temperature. The pH of the mixture was adjusted to about 9 by the addition of 20% sodium hydroxide and the mixture was extracted with 4×250 ml. of ethyl acetate. The combined ethyl acetate extracts were re-extracted with 4×300 ml. of 1% sodium hydroxide and the aqueous extracts were added to a mixture of 500 g. of ice and 300 ml. of 6 N hydrochloric acid. The precipitate which formed upon standing at room temperature overnight was collected to give 91.0 g. (78%) of the alkylbarbituric acid, m.p. 112°–114°.

EXAMPLE 3

5-Allyl-5-(1-carboxy-isopropyl)barbituric acid

A mixture of 50 g. of 5-allyl-5-(1-ethoxycarbonyl-isopropyl)barbituric acid and 400 ml. of 1 N hydrochloric acid was heated under reflux for 4 hours. The solution was allowed to stand at room temperature overnight and the precipitate was collected to yield 42.5 g. (94%) of the acid, m.p. 202°–203°.

EXAMPLE 4

5-Allyl-5-(1-p-nitrophenyloxycarbonyl-isopropyl)barbituric acid

A solution of 2.19 g. of ethyl chloroformate in 90 ml. of chloroform was added to a solution of 5.08 g. of "allonalcarboxylic acid" [5-allyl-5-(1-carboxy-isopropyl)barbituric acid] and 2.02 g. of triethylamine in 100 ml. of dichloromethane, cooled to 0°-5°, and the mixture was stirred at room temperature for 5 hours. p-Nitrophenol (3.06 g.) was added and the mixture was stirred at room temperature for 14 hours. The reaction mixture was washed with saturated sodium carbonate solution (3×25 ml.), and water until the workings were neutral, dried over anhydrous sodium sulfate and filtered. Evaporation of the filtrate under reduced pressure gave 4.7 g. of an oil. Crystallization from a mixture of ether-heptane (1:1) gave 2.2 g. of the ester, m.p. 140°-141°.

EXAMPLE 5

5-Propyl-5-(p-aminophenyloxycarbonyl-isopropyl)barbituric acid

A solution of 750 g. of 5-allyl-5-(p-aminophenyloxycarbonyl-isopropyl)barbituric acid in 15 ml. of ethanol containing 100 mg. of 10% palladium-on-carbon as catalyst was subjected to hydrogenation at room temperature and atmospheric pressure. After one hour, the required amount (180 ml.) of hydrogen had been taken up. The reaction mixture was filtered through Celite, and the filtrate was evaporated to dryness. The residue was chromatographed on 13 g. of silica gel with ethyl acetate as the eluent. Fractions containing the desired product were evaporated. The remaining solid was recrystallized from chloroform/ether to afford 620 mg. (89%) of the ester, m.p. 212°-215°.

EXAMPLE 6

5-Allyl-5-[1-(4-aminobutylcarbamoyl)-isopropyl]barbituric acid

A mixture of 2.5 g. of 5-allyl-5-(1-carboxy-isopropyl)-barbituric acid, 1.95 g. of 1,1'-carbonyldiimidazole and 100 ml. of tetrahydrofuran was stirred under nitrogen at room temperature for 3 hours. To the solution was added 4.5 g. of 1,4-diaminobutane and the mixture was stirred overnight. The gummy solids were decanted and suspended in hot tetrahydrofuran. The crystalline material was collected, yield 1.8 g. of the amide, m.p. 160°-165°. A sample recrystallized from ethanol melted at 170°.

5-Allyl-5-[1-(3-aminopropylcarbamoyl)-isopropyl]-barbituric acid was prepared from 2.5 g. of 5-allyl-5-(1-carboxy-isopropyl)barbituric acid, 2 g. of 1,1'-carbonyldiimidazole, 100 ml. of tetrahydrofuran and 4 g. of 1,3-diaminopropane by the above procedure. The product melted at 202°-203°.

EXAMPLE 7

Preparation of latex polymers of aminoaryl esters and amino-lower alkyl amides of carboxy substituted barbiturates—general procedure 5-Allyl-5-[1-(4-aminobutylcarbamoyl)-isopropyl]barbituric acid is reacted with a latex suspension in the presence of 1-cyclohexyl-3-(2-morpholino-ethyl)carbodiimide metho-p-toluenesulfonate or 1-ethyl-3-(3-dimethylaminopropyl)carbodiimide hydrochloride. The resultant complex is washed by repeated sedimentation of the solid latex particles by centrifugation and resuspension in an appropriate buffer until no free aminobutylbarbituric acid is left in the aqueous phase of the suspension. The aminobutylbarbituric acid is used at a concentration of 1 mg. per ml. in distilled water. The solution is adjusted to pH 5.0. The latex suspension is a carboxylated styrene butadiene copolymer (Fluka No. 241), which has been washed and then diluted in water to contain approximately 8% latex solids. The concentration of the carbodiimide used is 1% weight/volume in distilled water. The reaction mixture is comprised of the following ratio of reactants: one volume of 1% carbodiimide, one volume of aminobutylbarbituric acid and three volumes of latex polymer suspension. The reaction is allowed to proceed at room temperature for 2-16 hours under continuous agitation. The solid polymer complex is then sedimented by centrifugation, washed with water and resuspended in 0.1 M TRIS saline buffer, pH 7.3 to a final concentration of 4 mg solids/ml.

Latexes such as Dow 816, Dow 421 and Dow batch 1721 may be employed instead of Fluka No. 241 and acetonitrile may be used as the solvent in the coupling reaction when 5-propyl-5-(1-p-aminophenyloxycarbonyl-isopropyl)barbituric acid is employed as the barbituric acid derivative.

EXAMPLE 8

Preparation of antiserum for test

Rabbit antiserum against barbiturates, prepared as described in U.S. Pat. No. 3,766,162, is diluted in an appropriate buffer system. This diluent consists of the following in aqueous solution at pH 7.3:
1. 0.01% Thimersol
2. 1% Normal rabbit serum
3. 0.01% EDTA [Ethylene diamine tetraacetate in the disodium form]
4. TRIS [0.1 Molar Tris(hydroxymethyl)aminomethane Hydrochloride]
5. 0.85% Sodium chloride.

EXAMPLE 9

Test Methodology

Two ml. of diluted antiserum prepared as in Example 8 is dispensed into small test tubes 10×75 mm. To this quantity is added 400-500 microliters of barbiturate free urine. The two fluids are mixed and left to incubate at 37° C. for 10 minutes. Ten microliters of diluted aqueous 5-allyl-5-[1-(4-aminobutylcarbamoyl)-isopropyl]-barbituric acid latex suspension containing approximately 0.3% latex solids by weight are added and mixed with the antiserum and urine. The test tubes are then placed into a 37° C. water bath or heat block so that approximately 1.5 cm of the liquid column in the test tube is underwater or inside the metal block. The appearance of the liquid in the tubes is transluscent, turbid, or slightly milky. For negative samples fine floccules are visible in the tube during the first hour. Large, easily visible floccules become evident during the second hour of incubation and tend to settle out leaving the liquid increasingly more clear and transparent.

The dilution of a particular antiserum which is chosen for the test system is the one which has the highest dilution while still producing a strong flocculation after 2 hours, as described above. When various amounts of barbiturates are dissolved in barbiturate free normal urine and substituted for the barbiturate free urine in the test systems, no flocculation occurs. The amount of barbiturate required to inhibit the flocculation will usually vary from 100 nanograms per ml. or greater depending on the concentration of antiserum used and the strength of the antiserum produced in the donor animal. It is also dependent on the amount of body fluid added. Thus, for the system described above, 400–500 μl of urine containing 200–300 nanograms of barbiturate/ml. is just sufficient to inhibit flocculation. 100 μl of urine containing 800–1000 nanograms/ml. or 50 μl of urine containing 1600–2000 nanograms/ml. will behave the same.

We claim:
1. The compound 5-allyl-5-[1-(4-aminobutyl)carbamoyl-isopropyl]barbituric acid.
2. The compound 5-allyl-5-[1-(3-aminopropyl)carbamoyl-isopropyl]barbituric acid.

* * * * *